United States Patent [19]

Edwards et al.

[11] 4,062,733
[45] Dec. 13, 1977

[54] RADIO-ASSAY OF OESTROGEN

[75] Inventors: John Christopher Edwards; Paul Hemesley, both of Amersham, England

[73] Assignee: The Radiochemical Centre Limited, England

[21] Appl. No.: 643,023

[22] Filed: Dec. 22, 1975

[30] Foreign Application Priority Data

Jan. 9, 1975 United Kingdom ............... 1012/75

[51] Int. Cl.² ...................... G01N 31/14; G01N 33/16
[52] U.S. Cl. ................................ 195/103.7; 23/230 B; 195/103.5 A
[58] Field of Search ...................... 195/103.7, 103.5 R, 195/103.5 A; 23/230 B

[56] References Cited

U.S. PATENT DOCUMENTS 3,654,090 4/1972 Schuurs et al. ............... 195/103.5 R
3,896,217 7/1975 Johnson ............................... 23/230 B

OTHER PUBLICATIONS

Hawker, Analytical Chemistry vol. 45 No. 11 pp.878–888 (1973).

Primary Examiner—Alvin E. Tanenholtz
Attorney, Agent, or Firm—Wenderoth, Lind & Ponack

[57] ABSTRACT

A method for the radio-assay of an oestrogen in a biological fluid which method comprises causing the oestrogen to compete with a radio-iodine derivative, selected from the group consisting of the 2-iodo-, 4-iodo- and 2,4-di-iodo- derivatives of the oestrogen, for reaction with a specific reagent for the oestrogen, separating the oestrogen and iodo-oestrogen bound to the specific reagent from the unbound oestrogen and iodo-oestrogen and measuring the radioactive concentration of one or both the bound and unbound fractions of oestrogen.

9 Claims, No Drawings

RADIO-ASSAY OF OESTROGEN

This invention relates to the use of radio-iodine derivatives of certain steroids in radio-assays for oestrogens. The steroids concerned are oestrogens, specifically oestriol — ($E_3$)
oestrone — ($E_1$)
oestradiol — ($E_2$)
oestetrol — ($E_4$)

and derivatives thereof for example the 16-glucuronide derivative. The compounds are 2-iodo, and 4-iodo, and 2,4-di-iodo derivatives of these oestrogens. The iodine includes an artificially high abundance of a radioactive iodine isotope, specifically I-131 or, more preferably, I-125.

These compounds can be prepared by well-known reactions. The oestrogens can be directly iodinated, using I-125 and chloramine-T, without prior conjugation to another substance. Thus, for example, Na I-125 and chloramine-T are added to the oestrogen in ethanolic solution and the solution mixed. After addition of sodium metabisulphite, the iodinated oestrogen derivative is extracted in organic solvent and purified by chromatography.

Oestriol exists in body fluids as a mixture of the unconjugated form with conjugates of which the most important are oestriol-3-hemisulphate; oestriol-16-glucuronide and oestriol-3-hemisulphate-16-glucuronide. Since it is normally desired to measure the total, rather than the free, oestriol, the only known radio-assay technique involves the following steps a. acid hydrolysis of the biological fluid to split oestriol conjugates;

b. extraction of total (free) oestriol into organic solvent and purification by chromatography;

c. saturation analysis of oestriol after removal of the organic solvent using a tritiated oestrogen derivative to compete with the oestriol for reaction with the specific reagent.

This procedure is subject to two main disadvantages. First tritium is a beta-emitter, and is much more difficult to detect and count than a gamma-emitter such as I-125. Second, organic extraction and chromatography is a tedious and time-consuming operation which cannot be contemplated when more than a few samples are to be assayed. Because of these disadvantages, oestriol is assayed in hospitals, not by a saturation analysis technique at all, but by the Kober Colour test which involves the inconvenience of collecting the patent's urine over a 24-hour period. It is one object of the invention to avoid the disadvantages of these existing tests.

The invention provides a method for the radio-assay of an oestrogen, e.g. oestriol, in a biological fluid, which method comprises causing the oestrogen to compete with a radio-iodine derivative of the oestrogen as hereinbefore defined for reaction with a specific reagent for the oestrogen, e.g. an antibody to the oestrogen, separating unbound oestrogen and iodo-oestrogen from oestrogen and iod-oestrogen bound to the specific reagent, and measuring the radioactive concentration of one or both of the bound and unbound fractions of oestrogen.

It is preferred that conjugated oestrogen, e.g. oestriol in the biological fluid be hydrolysed by means of enzyme rather than acid. Enzyme hydrolysis of oestriol conjugates is known and the two enzymes required, glucuronidase and aryl sulphatase are both commercially available. A great advantage of enzyme hydrolysis over acid hydrolysis is that the hydrolysate can be used for the assay without the need for solvent extraction of the oestrogen.

The antibody to the oestrogen may be produced by immunising, for example, rabbits, with the oestrogen-6-carboxymethyloxime-bovine serum albumin using published methods. Alternatively, the oestrogen may be conjugated in the 3- or 16- and/or 17- position.

In the assay, an accurately known volume of the biological fluid is incubated with a standard amount of the radio-iodinated oestrogen derivative and a standard amont of the specific reagent, e.g. antibody, insufficient to bind all the oestrogens present. The radio-iodinated oestrogen derivatives and the specific reagent may conveniently be provided in buffered solution containing horse serum. After equilibrium between bound and unbound oestrogens, for example between oestriol and the radio-iodinated derivatives, has been reached, the bound oestrogen may be precipitated by the addition of ammonium sulphate solution, or the free oestrogen removed from solution by adsorption with charcoal, and the mixture centrifuged. The radioactive concentration of the precipitate and/or the supernatant liquid is then counted by standard techniques. If an absolute determination is required, a calibration curve may be generated in the usual way by means of oestrogen, e.g. oestriol, solutions of known concentrations, conveniently also in horse serum. The range of concentrations of the oestrogens normally encountered are given in the following table.

| OESTROGEN | CONCENTRATION IN ng/ml | |
|---|---|---|
| | 'NORMAL' WOMEN | PREGNANT WOMEN |
| $E_1$ | 0 – 5 | 0 – 200 |
| $E_2$ | 0 – 5 | 0 – 50 |
| $E_3$ | O – 5 | 0 – 500 |
| $E_4$ | Not present | 0 – 50 |

There is also provided in the invention, an assay kit for an oestrogen e.g. oestriol, which kit comprises:

a. a supply of a radio-iodine derivative of the oestrogen as hereinbefore defined, b. a supply of a specific reagent for the oestrogen, e.g. an antibody to the oestrogen, c. preferably, a supply of one or more enzymes for hydrolysing oestrogen conjugates, d. preferably, a supply of the oestrogen for use in preparing standards, e. preferably, ammonium sulphate for precipitating bound oestrogen, and f. preferably, tubes for performing the assay.

The radio-iodine derivatives and the specific reagent, e.g. antibody may each be supplied in buffer solution containing a bacteriostat, e.g. sodium azide or thiomersal.

The following Examples illustrate the invention.

EXAMPLE 1

A. IODINATION OF OESTRIOL

Chloramine-T (0.5 mg in 100 μl water) is added to a stirred mixture of oestriol (50 μg in 400 ul ethanol) and Na$^{125}$I (10mCi in 100 μl dilute NaOH), and the mixture is stirred for a further 5 minutes. Sodium metabisulphite (1.2 mg in 500 μl water) is then added and the mixture stirred for 5 minutes before 1 ml of 0.1 M HCl is added. The mixture is then vigorously stirred with 1 ml of chloroform. The aqueous layer is separated from the organic solvent, and the aqueous layer is re-extracted with a further 1 ml of chloroform. The pooled chloroform extracts are evaporated to dryness under a stream of nitrogen, and the residue is redissolved in 50 µl of ethanol. The ethanol solution of $^{125}I$ — labelled oestriol derivative is purified by chromatography and the product is diluted in phosphate buffer containing horse serum (10%), sodium azide (1 mg/ml) and gelatine (1 mg/ml) prior to use in the radioimmunoassay Oestrone, oestradiol, oestetrol and oestriol-16- -($\beta$-D-glucuronide) were iodinated using the method described above. The yields were as follows:

| OESTROGEN | % RADIOCHEMICAL YIELD |
| --- | --- |
| Oestrone | 55.3 |
| Oestradiol | 44.6 |
| Oestetrol | 87.8 |
| Oestriol-16- -($\beta$-D-glucuronide) | 17.9 |

B. RADIOIMMUNOASSAY OF OESTRIOL

Samples of 50 µl of standard solutions of oestriol in horse serum, or of the unknown human serum samples, are dispensed into plastic tubes. To each tube is added 200 µl of a solution of enzymes (extracted from the snail Helix pomatia) in sodium acetate buffer, pH 5, and the contents of the tubes are briefly mixed. The tubes are then stoppered and incubated in a water bath at 37° C for 2 hours. After the incubation, replicate 50 µl samples are taken from the hydrolysed serum and dispensed into plastic tubes. to each tube is added 200 µl of phosphate buffer containing 10% horse serum, sodium azide (1 mg/ml) gelatine (1 mg/ml), and the oestriol derivative labelled with $^{125}I$ as described above (approximately 0.3 µCi/ml). Volumes of 200 µl of the phosphate buffer containing horse serum, sodium azide and gelatine, and containing a dilution of antiserum produced against oestriol conjugated to albumin are added to each tube, and the contents of the tubes are then mixed. The tubes are left at ambient temperature for 30 minutes, and 500 µl of an ammoniumm sulphate solution (5.4 g in 10 ml water) is then added to each tube. After mixing, the tubes are centrifuged, the supernatant liquid is removed by aspiration and the precipitates in the tubes are counted in a $\gamma$-counter.

| Anti serum | Totals c.p. 100 secs. | Standard Curves | | | | | |
| --- | --- | --- | --- | --- | --- | --- | --- |
| | | | % Bound. | | | | |
| | | Co | 50 ngE$_3$ | 100 ngE$_3$ | 200 ngE$_3$ | 350 ngE$_3$ | 500 ngE$_3$ |
| A | 111,169 | 68.2 | 57.2 | 47.3 | 32.6 | 23.0 | 17.5 |
| B | 111.169 | 69.8 | 55.2 | 47.3 | 33.0 | 21.4 | 17.3 |

EXAMPLE 2

RADIOIMMUNOASSAY OF OESTRONE

Oestrone was assayed by the method described in Example 1 but in which the antiserum was produced by immunising with (a) oestrone-6-carbomethoxyoxime thyroglobulin (source Miles-Yeda) and (b) an oestrone derivative coupled in the 6 position (source, The John Radcliffe Hospital, Oxford).

| Antiserum | Dilution of antiserum | Standard Curves | | | |
| --- | --- | --- | --- | --- | --- |
| | | Totals c.p. 100 secs. | Age label | % Bound | |
| | | | | Co | 1ng oestrone |
| Miles-Yeda | As supplied | 10,700 | 23 days | 40.1 | 15.4 |
| J.Radcliffe Hosp. | 1/32,000 | 19,300 | 30 days | 44.7 | 11.2 |

EXAMPLE 3

RADIOIMMUNOASSAY OF OESTRADIOL

Oestradiol was assayed by the method given in Example 1 but in which the antiserum was produced by immunising with (a) oestradiol-6-carbomethoxyoxime-BSA (source Miles-Yeda) and (b) an oestradiol derivative coupled in the 6 position (source The John Radcliffe Hospital, Oxford).

| Antiserum | Dilution of antiserum | Standard Curves | | | | |
| --- | --- | --- | --- | --- | --- | --- |
| | | Totals c.p. 100 secs. | Age label | % Bound | | |
| | | | | Co | 1ng E$_2$ | 2ng E$_2$ |
| Miles-Yeda | As supplied | 8,100 | 23 days | 26.9 | 4.0 | — |
| J.Radcliffe | 1/3200 | 14,000 | 30 days | 51.5 | 3.0 | 0.5 |
| J.Radcliffe | 1/640 | 140,000 | 31 days | 79.6 | 32.7 | 13.1 |

EXAMPLE 4

RADIOIMMUNOASSAY OF OESTETROL

Oestetrol was assayed by the method described in Example 1 using antiserum produced by immunising with oestriol-6-carbomethoxyoxime-BSA as the specific reagent, as an antiserum to oestetrol was not available.

| Antiserum | Dilution of antiserum | Standard Curves. Totals 132,800 c.p. 100 secs. (Age label 7 days) | |
| --- | --- | --- | --- |
| | | % Binding Co | % Binding in presence of 20ng E$_4$ |
| A | 1/100 | 58.5 | 11.0 |
| B | 1/100 | 48.7 | 8.1 |

EXAMPLE 5

A KIT FOR THE RADIOIMMUNOASSAY OF OESTRIOL (E$_3$)

The kit comprises the following:

a. 5 vials of freeze dried E$_3$ in horse-serum which when reconstituted will give standard solutions of the following approximate concentrations — 0, 30, 80, 200 and 400 ng/ml.

b. 1 vial containing approximately 13 mls of a solution of $^{125}I$ - E$_{13}$ in phosphate buffer, the concentration being 0.3µ Ci/ml.

c. 1 vial containing approximately 6.5 ml of enzyme solution for hydrolysis of oestriol conjugates.

d. 1 vial containing approximately 13 ml of a solution of an anti-oestriol serum.

e. 1 vial containing approximately 16 g of ammonium sulphate (solid).

f. 30 polystyrene tubes 55 × 12 mm (capacity approximately 5 mls) for use in the enzyme hydrolysis step.

g. 1 expanded polystyrene test tube rack;

h. 1 set of instructions for the assay based on the method given in Example 1.

What is claimed is:

1. A method for the radio-assay of an oestrogen in a biological fluid which method comprises
   a. causing said oestrogen to compete with a radio-iodine derivative, selected from the group consisting of the 2-iodo-, 4-iodo- and 2,4-di-iodo- derivatives of said oestrogen for reaction with a specific antibody to the oestrogen,
   b. separating the oestrogen and iodo-oestrogen bound to the specific antibody from the unbound oestrogen and iodo-oestrogen and
   c. measuring the radioactive concentration of one or both of the bound and unbound fractions of oestrogen.

2. The method as claimed in claim 1 in which there is an additional step preceding (a) in which conjugated oestrogens are hydrolysed.

3. The method as claimed in claim 2 in which the hydrolysis step is carried out enzymatically.

4. The method as claimed in claim 1, wherein the specific reagent is an antibody to the specific oestrogen.

5. The method as claimed in claim 1, in which the specific antibody is specific to oestrogen-6-carboxymethyloxime-BSA.

6. The method as claimed in claim 1, wherein the oestrogen is oestriol.

7. A kit for carrying out radio-assays of an oestrogen by the method of claim 1, which kit comprises,
   i. a supply of a buffered solution of a radio-iodo derivative selected from the group consisting of the 2-iodo-, 4-iodo- and 2, 4-di- iodo derivatives of said oestrogen
   ii. a supply of a specific antibody to the oestrogen.

8. A kit as claimed in claim 7 in which at least one enzyme for liberating the oestrogen by hydrolysis of conjugates thereof is additionally supplied.

9. A kit as claimed in claim 8 in which samples of the oestrogen for preparing standards are additionally supplied.

* * * * *